(12) United States Patent  
Morancho Rodríguez et al.

(10) Patent No.: US 8,626,464 B2  
(45) Date of Patent: Jan. 7, 2014

(54) DIMENSIONAL INSPECTION METHOD FOR A COMPOSITE PART

(75) Inventors: Josep Morancho Rodríguez, Madrid (ES); Nuria Rodrigo Caballero, Madrid (ES)

(73) Assignee: Airbus Operations S.L., Madrid (ES)

( * ) Notice: Subject to any disclaimer, the term of this patent is extended or adjusted under 35 U.S.C. 154(b) by 305 days.

(21) Appl. No.: 13/073,734

(22) Filed: Mar. 28, 2011

(65) Prior Publication Data

US 2012/0101757 A1    Apr. 26, 2012

(30) Foreign Application Priority Data

Oct. 26, 2010 (ES) .................................. 201031564

(51) Int. Cl.
*G06F 19/00* (2011.01)

(52) U.S. Cl.
USPC .......................................................... 702/81

(58) Field of Classification Search
USPC .......................................................... 702/81
See application file for complete search history.

(56) References Cited

U.S. PATENT DOCUMENTS 4,325,640 A    4/1982  Dreyfus et al.
2005/0159840 A1    7/2005  Lin et al.

FOREIGN PATENT DOCUMENTS

DE    10 2007 048 588 A1    4/2009
EP    0 199 961 A2    12/1986

OTHER PUBLICATIONS

Bernd Bickel, Design and Fabrication of Materials with Desired Deformation Behavior, ACM Transactions on Graphics, vol. 29, No. 4, Article 63, Publication date: Jul. 2010., p. 63:1-63:10.*

* cited by examiner

*Primary Examiner* — Tung S Lau
(74) *Attorney, Agent, or Firm* — Birch, Stewart, Kolasch & Birch, LLP

(57) ABSTRACT

A method for performing a dimensional inspection of a fabricated composite part (9), comprising steps of: a) Providing a number of points ($I_{ij}$, $O_{ij}$) to be inspected in its inner and outer surface; b) Obtaining the positional data of said points ($I_{ij}$, $O_{ij}$) from the fabricated composite part (9) hold in a position that allows the access to its outer and inner surfaces as a first set of positional data ($WI_{ij}$, $WO_{ij}$); c) Using said first set of positional data ($WI_{ij}$, $WO_{ij}$) and a second set of positional data ($TI_{ij}$, $TO_{ij}$) of the same points ($I_{ij}$, $O_{ij}$) obtained from an analytical model defining its theoretical geometry for calculating the deviations between them taking into account the deformations suffered by the fabricated composite part (9) in said position. The invention also refers to a workstation (11) for performing the method.

15 Claims, 2 Drawing Sheets

DIMENSIONAL INSPECTION METHOD FOR A COMPOSITE PART

FIELD OF THE INVENTION

The present invention refers to a dimensional inspection method of fabricated composite parts and, more particularly, to a dimensional inspection method of large composite parts such as a wing cover of an aircraft. The invention also refers to a workstation to carry out said dimensional inspection method.

BACKGROUND OF THE INVENTION

Dimensional inspection techniques shall be used in the fabrication process of, particularly, large composite parts, i.e. parts made out with composite materials consisting of fibers or fiber bundles embedded in a matrix of thermosetting or thermoplastic resin, such as aircraft wing covers, to assure that the dimensional and geometrical features of the fabricated part do not deviate from its nominal values by more than a predetermined amount.

Since the acceptability and reliability of a composite part can be affected if said features do not conform to design objectives, it is necessary to perform a detailed dimensional inspection in the final stage of the fabrication process.

In the prior art, the dimensional inspection of a large composite part is usually done in the curing tool using a manual laser interferometer and assuming that the curing tool surface is the nominal or theoretical composite part outer surface, i.e. the aerodynamic surface in the case of aircraft wing covers. In this respect, vacuum is used to push the composite part inner surface to the curing tool surface in order to overcome the deformations that may appear after the curing cycle. Deviations are calculated by comparing directly the distance from a number of selected points in the inner surface to the curing tool surface with the corresponding nominal distance.

However, the assumption that the curing tool surface can be used as the nominal outer surface of the composite part, as it has been seen in several tests, is erroneous: the curing tool may not follow exactly the nominal outer surface due to machining deviations and/or to level problems and the vacuum power may not be enough to overcome the stiffness of the part. Consequently the dimensional inspection results are not as accurate as is needed.

The present invention focuses on finding a solution for these drawbacks.

SUMMARY OF THE INVENTION

An object of the present invention is to provide a method for performing a dimensional inspection of a fabricated composite part that assures high accuracy degree results.

Another object of the present invention is to provide a method for performing a dimensional inspection of a fabricated composite part to be performed out of the autoclave, where its manufacturing process ends, for reducing costs.

Another object of the present invention to provide a suitable workstation for performing a dimensional inspection of a fabricated composite part.

In one aspect, said objects are met by providing a method for performing a dimensional inspection of a fabricated composite part, preferably a part belonging to a vehicle, and more preferably to an aircraft, comprising steps of:

a) Providing a number of points $I_{ij}$, $O_{ij}$ to be inspected in its inner and outer surface;

b) Obtaining the positional data of said points $I_{ij}$, $O_{ij}$ from the fabricated composite part hold in a position that allows the access to its outer and inner surfaces as a first set of positional data $WI_{ij}$, $WO_{ij}$;

c) Using said first set of positional data $WI_{ij}$, $WO_{ij}$ and a second set of positional data $TI_{ij}$, $TO_{ij}$ of the same points $I_{ij}$, $O_{ij}$ obtained from an analytical model of said composite part defining its theoretical geometry for calculating the deviations between the geometry of the fabricated composite part and its theoretical geometry, said calculation being made so that the deformations suffered by the fabricated composite part in said position that allows the access to its outer and inner surfaces are corrected.

In a preferred embodiment, in step a) said plurality of points $I_{ij}$, $O_{ij}$ are distributed in a number of transversal sections R, of said fabricated composite part. Hereby it is achieved a dimensional inspection method adapted to the needs of composite parts.

In another preferred embodiment said step c) comprises, for each of said transversal sections R, the following substeps: c1) obtaining, for the fabricated composite part and for its theoretical geometry, curves defining the shape of the outer surface and the position $P_{ij}$, $P'_{ij}$ of the points $I_{ij}$ in the inner surface; c2) developing said curves 31, 33 into a common reference plane 35, dragging to them the position $P_{ij}$, $P'_{ij}$ of the points $I_{ij}$ in the inner surface and calculating the deviations $\delta_{ij}$ between them. Hereby it is achieved a highly efficient method for obtaining the desired results of a dimensional inspection.

In another preferred embodiment, the fabricated composite part is an aircraft wing cover comprising a skin and a plurality of stringers, the distribution of said points $I_{ij}$, $O_{ij}$ to be scanned being arranged for providing sufficient positional information for calculating at least the deviations of one or more of the following parameters: skin thickness along the wing cover sections were the ribs will be attached; stringers web height along the wing cover sections were the ribs will be attached; stringers foot height along the wing cover sections were the ribs will be attached. Hereby it is achieved a highly efficient dimensional inspectional method for an aircraft wing cover.

In another aspect the above mentioned objects are met by providing a workstation for performing a dimensional inspection of a fabricated composite part according to the above-mentioned method comprising:

a jig for supporting the fabricated composite part in a vertical position;

two probes for obtaining positional data $WI_{ij}$, $WO_{ij}$ of a plurality of points $I_{ij}$, $O_{ij}$ located in the inner and outer surfaces of said fabricated composite part installed on two robots having guiding means along two axis H, V for approaching said probes to said plurality of points $I_{ij}$, $O_{ij}$;

communication means for communicating said positional data $WI_{ij}$, $WO_{ij}$ to a computer system.

Other characteristics and advantages of the present invention will be clear from the following detailed description of embodiments illustrative of its object in relation to the attached figures.

DETAILED DESCRIPTION OF THE INVENTION

The detailed description of the present invention will refer to the dimensional inspection of an aircraft wing cover 9 made out with composite materials.

The basic idea of the present invention is performing the dimensional inspection of the aircraft wing cover 9 out of the curing tool used in the final stage of its fabrication process, having the aircraft wing cover 9 in a vertical position so as to be able to scan its inner and outer surfaces, and comparing the dimensional inspection results with the expected results in an efficient and accurate manner.

Figure 1:
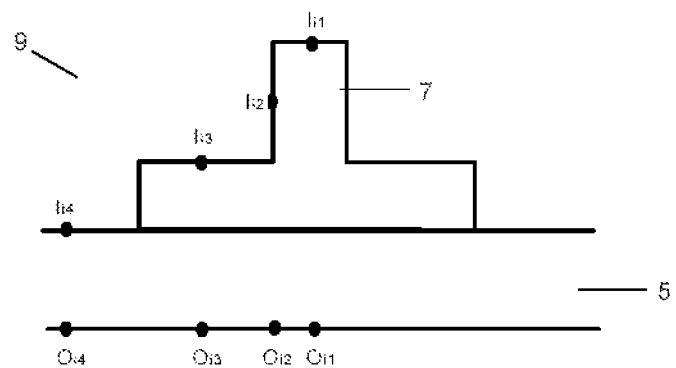
FIG. 1 is a partial view of a transversal section of an aircraft wing cover illustrating the position of points to be scanned according to the present invention.

The key steps of the dimensional inspection method according to the present invention are the following:

Providing a scanning plan of the aircraft wing cover 9, i.e. a number of points $I_{ij}$ in its inner surface and a number of points $O_{ij}$ in its outer surface where positional data shall be obtained. The distribution of said points $I_{ij}$, $O_{ij}$ shall be made in accordance to the objectives of the inspection. The geometrical parameters to be inspected would typically include at least the skin thickness and the stringer web and foot height in the aircraft wing cover sections were the ribs or other structural elements will be attached and, as well, the skin thickness in other relevant locations. Consequently, as seen in the partial view of a transversal section $R_i$ of the wing cover 9 shown in FIG. 1 corresponding to a preferred embodiment, said distribution will include points such as the points $O_{i1}$, $O_{i2}$, $O_{i3}$, $O_{i4}$ in is outer surface and the points $I_{i1}$, $I_{i2}$, $I_{i3}$, $I_{i4}$ in its inner surface that allow to measure the thickness of the skin 5 and the heights of the web and the foot of the stringer 7. In the case of an aircraft wing cover 9 of an span of, for instance 33 m, the number of points $I_{ij}$, $O_{ij}$ to be scanned in both sides may amount to 8000. The sub-index i is then used for indicating the number of a transversal section of the aircraft wing cover 9 with respect to axis H in FIG. 2 and the sub-index j is used for numbering the points within said transversal section. It is therefore a reference system adapted to said preferred embodiment but as the skilled man will readily understand any other suitable reference system can be used.

Obtaining the positional data of said points $I_{ij}$, $O_{ij}$ in the aircraft wing cover 9 hold in a vertical position in a dimensional inspection workstation 11 as a first set of positional data $WI_{ij}$, $WO_{ij}$ (for instance x, y, z coordinates of said points $I_{ij}$, $O_{ij}$).

Obtaining the positional data of said points $I_{ij}$, $O_{ij}$ from an analytical model defining the theoretical geometry of the aircraft wing cover 9 as a second set of positional data $TI_{ij}$, $TO_{ij}$ (using the same coordinate system than for $WI_{ij}$, $WO_{ij}$) and comparing both sets of data $WI_{ij}$, $WO_{ij}$; $TI_{ij}$, $TO_{ij}$ to obtain the deviations between the fabricated aircraft wing cover 9 and its theoretical geometry taking into account that the first set of data $WI_{ij}$, $WO_{ij}$ is obtained in a workstation 11 that causes deformations in the aircraft wing cover 9 because it can only grab the aircraft wing cover 9 in a few sections to give access to the scanning tools all along inner and outer surfaces of the aircraft wing cover 9.

We will now proceed to a description of a preferred embodiment of the method and the workstation according to the present invention.

Figure 2:
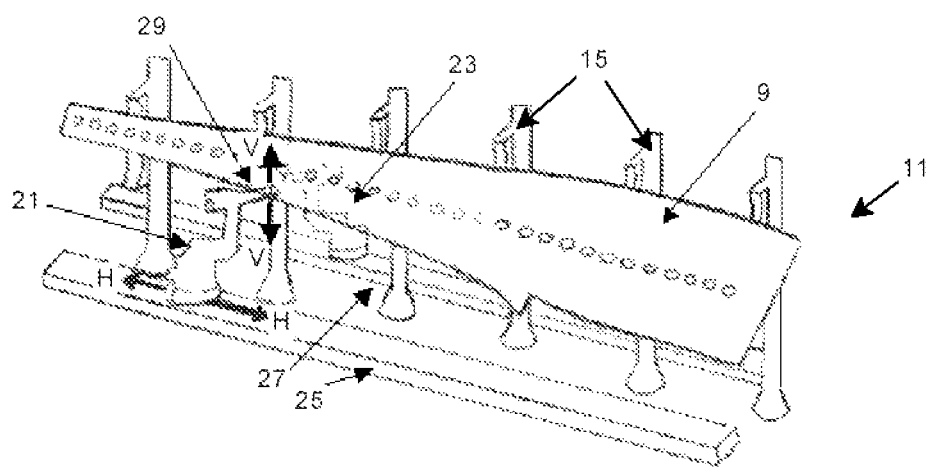
FIG. 2 shows a schematic perspective view of a dimensional inspection workstation of an aircraft wing cover according to the present invention.

Following FIG. 2 it can be seen that the workstation 11 includes, on one side, a number of arms 15 for holding the aircraft wing cover 9 in a vertical position and, on the other side, robots 21, 23 (for instance KUKA Robots KR210L100-2K) that are installed in linear guides 25, 27 with probes 29 such as laser interferometers (for instance a Leica Absolute Tracker AT-901 LR) for collecting positional data of points located, respectively, in the inner and outer surface of the aircraft wing cover 9. Said robots 21, 23 may translate horizontally as indicated by arrows H and its probes 29 can scan points in the aircraft wing cover inner and outer surfaces following vertical paths as indicated by arrows V.

The displacement of said robots probes 29 as they follow the inner and outer surfaces of the aircraft wing cover 9 is detected using suitable means and its output is transmitted to a computer system (not shown in FIG. 2) through a suitable communication link. Data indicating a relative position of probes 29 along the aircraft wing cover 9 may be transmitted to said computer system where it will used for obtaining dimensional parameters of aircraft wing cover 9.

Figure 3:
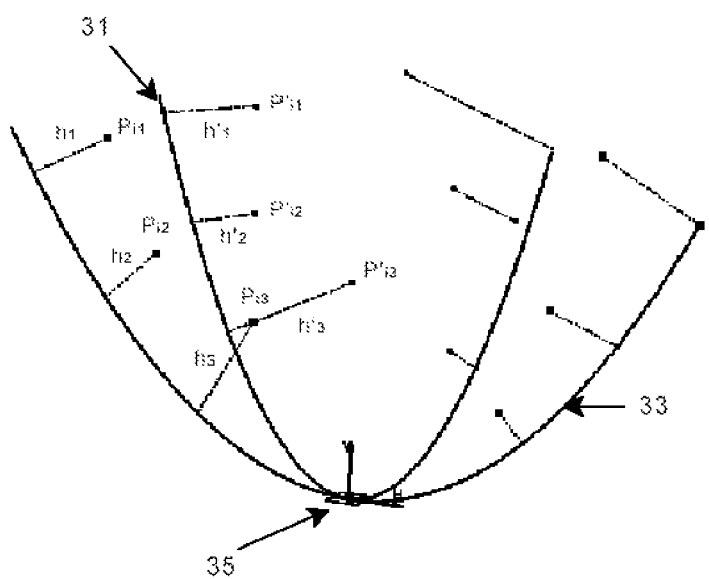
FIG. 3 is a sketch showing the theoretical aircraft wing cover section and the corresponding wing cover section resulting from the scanning data obtained in the dimensional inspection of the fabricated aircraft wing cover.

FIG. 3 shows a curve 31 corresponding to the outer surface of the aircraft wing cover 9 in one transversal section R scanned with said probes 29 and the position of three points $P'_{i1}$, $P'_{i2}$, $P'_{i3}$ in the inner surface at distances h'1, h'2, h'3 from the outer surface. Said curve 31 is obtained processing the positional information $WO_{i1}$, $WO_{i2}$, $WO_{i3}$, . . . provided by the workstation 11 of the scanned points $O_{i1}$, $O_{i2}$, $O_{i3}$, . . . in the outer surface of the aircraft wing cover 9 by any suitable mathematical method, for example, a regression analysis. The position of said points $P'_{i1}$, $P'_{i2}$, $P'_{i2}$ is obtained processing the positional information $WI_{i1}$, $WI_{i2}$, $WI_{i3}$ provided by the workstation 11 of the scanned points $I_{i1}$, $I_{i2}$, $I_{i3}$, . . . in the inner surface of the aircraft wing cover 9.

FIG. 3 also shows a curve 33 corresponding to the nominal outer surface of aircraft wing cover 9 in the same transversal section R and the position of the points $P_{i1}$, $P_{i2}$, $P_{i3}$ in the inner surface at distances h1, h2, h3 from the outer surface. Said curve 33 is obtained processing the positional information $TO_{i1}$, $TO_{i2}$, $TO_{i3}$, . . . provided by the analytical model of the aircraft wing cover with respect to the points $O_{i1}$, $O_{i2}$, $O_{i3}$, . . . in the outer surface of the aircraft wing cover 9 by any suitable mathematical method, for example, a regression analysis. The position of said points $P_{i1}$, $P_{i2}$, $P_{i3}$ is obtained processing the positional information $TI_{i1}$, $TI_{i2}$, $TI_{i3}$ provided by the analytical model of the aircraft wing cover 9 with respect to the points $I_{i1}$, $I_{i2}$, $I_{i3}$, . . . in the inner surface of the aircraft wing cover 9.

Figure 4:
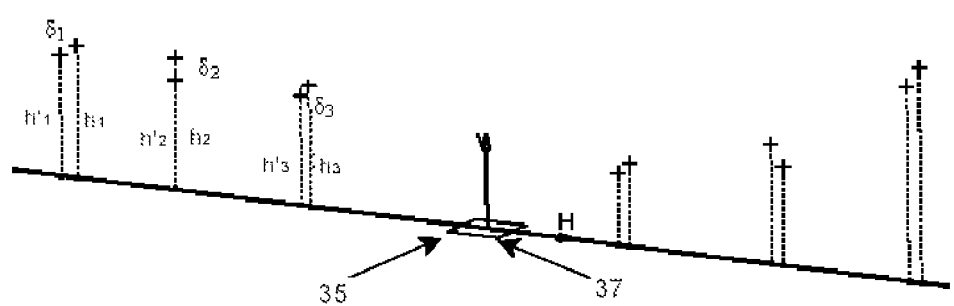
FIG. 4 is a sketch showing said aircraft wing cover sections developed in a common reference plane.

FIG. 4 shows said curves 31, 33 and the points $P'_{i1}$, $P'_{i2}$, $P'_{i3}$, $P_{i1}$, $P_{i2}$, $P_{i3}$ developed on the common reference plane 35 with respect to a reference point 37 that allow an easy calculation of the deviations $\delta_1$, $\delta_2$, $\delta_3$ between them. As the skilled man will readily understand the calculation of said deviations is done by a suitable algorithm implemented in computer means.

In general terms, it is considered that the present invention is applicable to any composite part of a moving vehicle (having hence an outer aerodynamic surface) and preferably to large composite parts.

One advantage of the present invention is that it allows the reduction of the composite fabrication process lead time and costs as the dimensional inspection is not carried out in the autoclave which is a very expensive curing tool.

Although the present invention has been fully described in connection with preferred embodiments, it is evident that modifications may be introduced within the scope thereof, not considering this as limited by these embodiments, but by the contents of the following claims.

The invention claimed is:

1. A method for performing a dimensional inspection of a fabricated composite part (9) using a robotic workstation (11),
the method comprising steps of:
a) providing a number of points (Iij, Oij) to be inspected on inner and outer surfaces of the fabricated composite part (9);
b) obtaining positional data of said points (Iij, Oij) from the fabricated composite part (9) while the fabricated composite part (9) is being held in a position that allows access to the outer and inner surfaces of the fabricated composite part (9), the positional data of said points (Iij, Oij) serving as a first set of positional data (WIij, WOij);
c) using said first set of positional data (WIij, WOij) and a second set of positional data (TIij, TOij) of the same points (Iij, Oij) obtained from an analytical model of said composite part defining a theoretical geometry for calculating deviations ($\delta$ij) between an actual geometry of the fabricated composite part (9) and the theoretical geometry of the fabricated composite part (9),
wherein the step of calculating the deviations ($\delta$ij) between the actual geometry and the theoretical geometry of the fabricated composite part (9) is made so that deformations suffered by the fabricated composite part (9) in the position that allows the access to the inner and outer surfaces are corrected.

2. The method for performing a dimensional inspection of a fabricated composite part (9) according to claim 1, wherein in step a) said plurality of points $I_{ij}$, $O_{ij}$ are distributed in a number of transversal sections ($R_i$) of said fabricated composite part (9).

3. The method for performing a dimensional inspection of a fabricated composite part (9) according to claim 1, wherein said fabricated composite part (9) is a part of a body of a vehicle.

4. The method for performing a dimensional inspection of a fabricated composite part (9) according to claim 1, the workstation (11) comprising:
a jig for supporting the fabricated composite part (9) in a vertical position;
two probes (29) for obtaining positional data ($WI_{ij}$, $WO_{ij}$) of a plurality of points ($I_{ij}$, $O_{ij}$) located in the inner and outer surfaces of said fabricated composite part (9) installed on two robots (21, 23) having guiding means along two axis (H, V) for approaching said probes (29) to said plurality of points ($I_{ij}$, $O_{ij}$);
communication means for communicating said positional data ($WI_{ij}$, $WO_{ij}$) to a computer system.

5. The method for performing a dimensional inspection of a fabricated composite part (9) according to claim 1, wherein the step of obtaining the positional data of said points ($I_{ij}$, $O_{ij}$) from the fabricated composite part (9) is accomplished without deforming the fabricated composite part (9).

6. The method for performing a dimensional inspection of a fabricated composite part (9) according to claim 2, wherein said step c) comprises, for each of said transversal sections ($R_i$) the following sub-steps:
c1) obtaining, for the fabricated composite part (9), curves (31, 33) defining an actual shape and a theoretical shape of the outer surface, and the position ($P_j$, $P'_j$) of the points ($I_{ij}$) in the inner surface;
c2) developing said curves (31, 33) into a common reference plane (35), dragging to said curves the position ($P_{ij}$, $P'_{1j}$) of the points ($I_{ij}$) in the inner surface, and calculating the deviations ($\delta_{ij}$) between the curves (31, 33).

7. The method for performing a dimensional inspection of a fabricated composite part (9) according to claim 2, wherein said fabricated composite part (9) is a part of the body of a vehicle.

8. The method for performing a dimensional inspection of a fabricated composite part (9) according to claim 2, the workstation (11) comprising:
a jig for supporting the fabricated composite part (9) in a vertical position;
two probes (29) for obtaining positional data ($WI_{ij}$, $WO_{ij}$) of a plurality of points ($I_{ij}$, $O_{ij}$) located in the inner and outer surfaces of said fabricated composite part (9) installed on two robots (21, 23) having guiding means along two axis (H, V) for approaching said probes (29) to said plurality of points ($I_{ij}$, $O_{ij}$);
communication means for communicating said positional data ($WI_{ij}$, $WO_{ij}$) to a computer system.

9. The method for performing a dimensional inspection of a fabricated composite part (9) according to claim 3, wherein said fabricated composite part (9) belongs to a wing or to an empennage of an aircraft.

10. The method for performing a dimensional inspection of a fabricated composite part (9) according to claim 3, the workstation (11) comprising:
a jig for supporting the fabricated composite part (9) in a vertical position;
two probes (29) for obtaining positional data ($WI_{ij}$, $WO_{ij}$) of a plurality of points (Iij, Oij) located in the inner and outer surfaces of said fabricated composite part (9) installed on two robots (21, 23) having guiding means along two axis (H, V) for approaching said probes (29) to said plurality of points ($I_{ij}$, $O_{ij}$);
communication means for communicating said positional data ($WI_{ij}$, $WO_{ij}$) to a computer system.

11. The method for performing a dimensional inspection of a fabricated composite part (9) according to claim 6, wherein said fabricated composite part (9) is a part of the body of a vehicle.

12. The method for performing a dimensional inspection of a fabricated composite part (9) according to claim 6, the workstation (11) comprising:
a jig for supporting the fabricated composite part (9) in a vertical position;
two probes (29) for obtaining positional data ($WI_{ij}$, $WO_{ij}$) of a plurality of points ($I_{ij}$, $O_{ij}$) located in the inner and outer surfaces of said fabricated composite part (9) installed on two robots (21, 23) having guiding means along two axis (H, V) for approaching said probes (29) to said plurality of points ($I_{ij}$, $O_{ij}$);
communication means for communicating said positional data ($WI_{ij}$, $WO_{ij}$) to a computer system.

13. The method for performing a dimensional inspection of a fabricated composite part (9) according to claim 9, wherein:
said fabricated composite part (9) is an aircraft wing cover (9) comprising a skin (5) and a plurality of stringers (7);
the distribution of said points ($I_{ij}$, $O_{ij}$) is arranged for providing positional information for calculating at least the deviations of one or more of the following parameters:
skin thickness along the aircraft wing cover sections where the ribs will be attached;
web height of the stringers along the aircraft wing cover sections where the ribs will be attached;
foot height of the stringers along the aircraft wing cover sections where the ribs will be attached.

14. The method for performing a dimensional inspection of a fabricated composite part (9) according to claim 9, the workstation (11) comprising:
- a jig for supporting the fabricated composite part (9) in a vertical position;
- two probes (29) for obtaining positional data ($WI_{ij}$, $WO_{ij}$) of a plurality of points ($I_{ij}$, $O_{ij}$) located in the inner and outer surfaces of said fabricated composite part (9) installed on two robots (21, 23) having guiding means along two axis (H, V) for approaching said probes (29) to said plurality of points ($I_{ij}$, $O_{ij}$);
- communication means for communicating said positional data ($WI_{ij}$, $WO_{ij}$) to a computer system.

15. The method for performing a dimensional inspection of a fabricated composite part (9) according to claim 13, the workstation (11) comprising:
- a jig for supporting the fabricated composite part (9) in a vertical position;
- two probes (29) for obtaining positional data ($WI_{ij}$, $WO_{ij}$) of a plurality of points ($I_{ij}$, $O_{ij}$) located in the inner and outer surfaces of said fabricated composite part (9) installed on two robots (21, 23) having guiding means along two axis (H, V) for approaching said probes (29) to said plurality of points ($I_{ij}$, $O_{ij}$);
- communication means for communicating said positional data ($WI_{ij}$, $WO_{ij}$) to a computer system.

* * * * *